United States Patent [19]

Engelbach et al.

[11] 4,031,135

[45] June 21, 1977

[54] MANUFACTURE OF ACRYLIC ACID BY OXIDATION OF PROPYLENE WITH OXYGEN-CONTAINING GASES IN TWO SEPARATE CATALYST STAGES

[75] Inventors: Heinz Engelbach, Limburgerhof; Richard Krabetz, Kirchheim; Gerd Duembgen, Dannstadt-Schauernheim; Carl-Heinz Willersinn, Ludwigshafen; Ulrich Lebert, Ludwigshafen; Fritz Thiessen, Ludwigshafen, all of Germany

[73] Assignee: BASF Aktiengesellschaft, Ludwigshafen (Rhine), Germany

[22] Filed: July 11, 1975

[21] Appl. No.: 595,321

[30] Foreign Application Priority Data

July 31, 1974 Germany ............... 2436818

[52] U.S. Cl. .................. 260/530 N; 260/533 N; 260/533 R; 260/597 R; 260/604 R
[51] Int. Cl.$^2$ .................................. C07C 51/32
[58] Field of Search ........ 260/533 N, 530 N, 604 R

[56] References Cited

UNITED STATES PATENTS 3,801,634  4/1974  Krabetz et al. ............... 260/533 N

FOREIGN PATENTS OR APPLICATIONS 939,713  10/1963  United Kingdom ........... 260/533 N Primary Examiner—Vivian Garner
Attorney, Agent, or Firm—Johnston, Keil, Thompson & Shurtleff

[57] ABSTRACT

In the oxidation of propylene to acrylic acid in the gas phase in two spatially separate oxidation stages, a part of the off-gas, which has been freed from condensable products, is fed to the oxidation stages in addition to freshly charged propylene and air, under the following conditions:

a. The recycled off-gas and air are in part fed to the first oxidation stage and in part to the second oxidation stage, b. The molar ratio of propylene : oxygen : residual gases fed to the first stage is 1 : 1.5–2.3 : 11–19, c. The molar ratio of the total propylene fed in, to the total oxygen fed in, in the form of air or off-gas, before and after the first stage, and to the total residual gases fed in is 1 : 1.9–2.5 : 13–25, with the proviso that d. The air and the recycled off-gas are divided between the two feed points in such a way that from 10 to 50% by volume of the total quantity of air and off-gas fed in are added after the first stage and e. The air and off-gas are admixed to the reaction gas mixture after the first stage, immediately after it leaves the catalyst zone, so that the mixture is rapidly cooled to a temperature of from 150° to 320° C.

3 Claims, No Drawings

MANUFACTURE OF ACRYLIC ACID BY OXIDATION OF PROPYLENE WITH OXYGEN-CONTAINING GASES IN TWO SEPARATE CATALYST STAGES

When the conventional process for the manufacture of acrylic acid by oxidation of propylene with oxygen-containing gases — which in most cases is carried out in two spatially separate catalyst stages — is operated industrially, it encounters a number of difficulties which hinder optimum performance of the process:

1. The concentrations or partial pressures of oxygen and propylene and the oxygen-propylene ratio in the synthesis gas must not exceed certain limits, firstly so as not to produce explosive mixtures and secondly to keep the combustion of propylene over the catalyst, which gives carbon monoxide and carbon dioxide, at a low level. On the other hand, with a low-oxygen-propylene ratio (e.g. a less than stoichiometric ratio) there is the danger of the catalyst being damaged by reduction, and at low oxygen and propylene concentrations and a low oxygen-propylene ratio the conversions and yields achievable at economically acceptable residence times are poor.

2. Depending on the operating conditions in the first catalyst stage, but also in those of the second catalyst stage, an uncontrollable "post-combustion" of the acrolein in the gas phase may occur in the material leaving the first and the second stage of the reactor. This post-combustion is, e.g., the more pronounced, (a) the higher is the partial pressure of oxygen and acrolein in the material leaving the reactor, (b) the higher is the temperature of the material leaving the reactor, which depends on the bath temperature and on the conversion achieved in the synthesis stages, (c) at times, the lower is the propylene conversion and (d) the longer is the residence time of the material leaving the reactor in the uncooled spaces which follow the catalyst beds.

3. The reaction products have a very marked tendency to polymerize in the condensed phase. Since the dew point of the reaction gas depends on the concentrations of water vapor, acrolein and acrylic acid, there is also a relationship between the polymerization problems and the operating conditions, quite apart from the effect of unsaturated or free-radical intermediates on the polymerization.

A method of achieving the object of carrying out the process safely on an industrial scale under optimum conditions in respect of yield, space-time yield, expense in isolating the acrylic acid in a pure form, and the like, must take into account the close interaction between difficulties, (1), (2) and (3). The fact is that the measures hitherto proposed only aim to eliminate one of the difficulties mentioned without taking into account its relation to the total process, thus arriving at imperfect partial solutions.

Thus, in the process of British Pat. No. 939,713, as in most conventional processes, steam in amounts of from 1 to 10 moles per mole of propylene is admixed as a diluent to the propylene-air mixture before the first stage and, if appropriate in addition to further air, to the reaction gas from the first stage before entering the second stage. It is true that the addition of steam produces an advantageous shift in the explosive limit and inhibits the combustion of propylene or acrolein over the catalysts to give carbon monoxide and carbon dioxide, but it does not inhibit the post-combustion of the acrolein in the space between, or after, the two catalyst stages. The conditions of the process as disclosed in Examples 1, 2 and 3, namely the high bath temperature used in the first stage (490° C or at least 350° C in the case of the preferred bismuth-containing catalyst, see page 2, line 77) and of the second stage (467° C or above 350° C, see claim), the low conversion of propylene and the oxygen content of the reaction gas containing acrolein, especially after admixture of further air before the second reactor, are such that in industrial operation a combustion of the acrolein in the space between the two catalyst stages is hardly avoidable, especially if the acrolein is recycled to a point before the second stage. A further disadvantage of the process is that as a result of the use of steam as an essential diluent under the conditions stated in the examples, and as a result of the low conversions of propylene and acrolein, the molar ratio of steam to acrylic acid in the off-gas from the second reactor is relatively high and hence the expense of isolating the acrylic acid in a pure form is correspondingly high.

The process of German Printed Application No. 1,793,302 uses pure oxygen as the oxidant. The off-gas from the second stage, after removing the acrylic acid, is employed as the requisite diluent for the propylene and the oxygen; this off-gas contains, as an inert component, the carbon monoxide and carbon dioxide and steam produced in the reaction and is recycled, after removing the products which can be condensed at from 100° to 120° C, to a point before the reactor, together with unconverted propylene, oxygen and acrolein. Under these conditions, selective control of the reaction so as to give acrylic acid, whilst remaining outside the explosive limits, is only possible either if considerable amounts of steam are used to dilute the fresh gases or if substantial amounts, compared to freshly fed propylene, of off-gas containing CO and $CO_2$ are recycled so as to achieve high $CO/CO_2$ concentrations, of from 20 to 89% by volume. In order that the mixture shall also remain outside the explosive limits and to keep the loss of oxygen low, it is essential to adjust the oxygen : propylene ratio to a low value - a less than stoichiometric value, according to the examples - of less than 1.5 : 1 in the synthesis gas. Viewed overall, the process of German Printed Application No. 1,793,302, which employs pure oxygen as the oxidant, is essentially restricted to the operating conditions specified in the examples (i.e. the following ratios: $H_2O$ : $C_3H_6$ =2 : 1; $O_2$ : $C_3H_6$ < 1.5 : 1; off-gas : fresh gas > 30 : 1) , which gives low conversion and low yields in a single pass (about 38 and 28 mole % respectively) and result in a dilute acrylic acid solution (from 21.6 to 34.6% strength by weight) being produced. It is true that as a result of the low oxygen : propylene ratio the hazard of a post-combustion of the acrolein after the first stage is less, but on the other hand the risk that as a result of the deficiency of oxygen unconverted propylene will reduce the catalyst and lower its selectiviy is increased (c.f., e.g., German Published Application No. 2,238,851, page 1, first paragraph). It is true that the known measure of combining both catalyst beds in immediate succession in a single reactor shell (cf. British Pat. No. 1,256,595) prevents post-combustion of the acrolein in the critical space between the catalyst beds, but this has the fundamental disadvantage that the two catalysts cannot be set separately to their respective optimum temperatures.

Some published patent applications therefore concern themselves with the problem of preventing the oxidation of the acrolein between the catalyst stages where these are spatially separate, without altering the basic processes, e.g. in respect of the operating conditions.

German Published Application No. 2,238,851 seeks to prevent post-combuston and polymerization by passing the hot reaction gas from the first stage, as it leaves the latter, directly into a heat exchange zone immediately connected thereto and cooling the gas therein indirectly to from 200° to 300° C with water of which the dew point is at least 25° above the dew point of the reaction mixture. Whilst this measure prevents polymerization, it does not entirely prevent post-combustion, since even in a heat exchanger operated in cocurrent the reaction gases are exposed to temperatures in the critical range, above from about 200° to 300° C, for a sufficiently long time. This is true particularly if the bath temperature of the first stage is high, as in Example 1 of German Published Application No. 2,238,851 (365° C) and the propylene conversion is low (less than 50%), so that the reaction gases leave the catalyst bed at a temperature which is above the bath temperature. Even if the process conditions or catalyst properties of the second stage demand a high bath temperature (385° C), as in Example 2, post-combustion may occur at the upper tube plate and at the tube entry points. A further disadvantage of this process is the expense entailed in fitting a heat exchanger between the two stages; it is true that the heat exchanger can be used to generate steam, but only at the cost of the conventional generation of steam in the second reactor, since the gas mixture which has been cooled in the interposed heat exchanger must again be heated to a reaction temperature above 200° to 300° C in the reaction tubes of the second stage.

A similarly unsatisfactory measure is that described in German Pat. No. 1,242,205, of passing the reaction gases, after leaving the reactor, through a bed of a solid inert material having a surface area greater than 31.5 m²/m³, and at the same time optionally inserting a heat exchanger, cooled by means of cold water, into the beds of inert material so as to cool the reaction gas to within 24° C above the dew point. This does not make it possible effectively to prevent post-combustion, as has already been shown in German Published Application Nos. 1,910,795 (page 1) and 2,238,851 (page 2, second paragraph and page 6, first paragraph), and polymerization of acrolein and acrylic acid may occur.

The measures described in German Published Application No. 1,910,795 are also exclusively directed to avoiding the post-reaction; in this case, the post-combustion is prevented by injecting an inert liquid, which vaporizes at the prevailing temperatures, into the reaction gases leaving the reactor. However, this produces dilute acrylic acid solutions if water is used, whilst if other liquids are used additional problems of separation arise, as indicated in German Published Application No. 2,238,851 (page 2, last paragraph).

It is an object of the present invention to provide a process for the manufacture of acrylic acid by catalytic oxidation of propylene in the gas phase in two spatially separate stages, in which the post-combustion between the two stages is avoided in a particularly simple and advantageous manner.

We have found that acrylic acid can be manufactured particularly advantageously by oxidation of propylene with gases containing molecular oxygen in two spatially separate oxidation stages by using the present new process in which an acrolein-selective catalyst, which at a bath temperature below 380° C and a residence time of up to 4 seconds is able to produce, in a single pass, a conversion of more than 80 mole% of the proplyene employed, is used in the first stage and a catalyst which is selective for acrylic acid and which at a bath temperature below 350° C and a residence time of up to 4 seconds is able to produce, in a single pass, a conversion of more than 80% of the acrolein, is used in the second stage, and in the oxidation a part of the off-gas, which has been substantially freed from condensable products, including water, and essentially consists of nitrogen and small amounts of unconverted propylene, oxygen, propane and carbon monoxide and dioxide is fed to the oxidation in addition to fresh propylene and air. In the new process (a) the recycled off-gas and air are in part fed to the first oxidation stage and in part to the second oxidation stage, b. the molar ratio of proplyene : oxygen : residual gases in the feed to the first stage is 1 : 1.5–2.3 : 11–19, c. the molar ratio of the total propylene fed in, to the total oxygen fed in, in the form of air or off-gas, before and after the first stage, and to the total residual gases fed in, is 1 : 1.9–2.5 : 13–25, with the proviso that d. the air and recycled off-gas are divided between the two feed points in such a way that from 10 to 50% by volume of the total quantity of air and off-gas fed in is added after the first stage, and e. the air and off-gas are admixed to the reaction gas mixture after the first stage, immediately after it leaves the catalyst zone, so that the mixture is rapidly cooled to a temperature of from 150° to 320° C.

The molar ratio (b) of propylene : oxygen : residual gases fed to the first stage is preferably 1 : 1.55–2.2 : 12–17, especially 1 : 1.6–2.1 : 12–16. The molar ratio (c) of total propylene fed in to total oxygen fed in, in the form of air and/or off-gas, before and after the first stage, to the total residual gases fed in, is preferably 1 : 2.0–2.45 : 15–24, especially 1 : 2.1–2.4 : 16–23, and the air and off-gas are preferably divided in accordance with (d) in such a way that from 20 to 45% by volume of the total amounts of air and off-gas fed in are added after the first stage.

The advantage of the process of the invention over the known processes is above all that a range of technical difficulties is overcome by virtually only one technological measure, namely by dividing the freshly fed air and the off-gas recycled, to dilute the synthesis gas, after separating off the acrylic acid (i.e. circulating gas) over the two stages. The direct heat exchange between the hot reaction gases from the first stage and the unheated off-gas and air fed in permits rapid quenching of the reaction gases to temperatures at which virtually no post-combustion of the acrolein occurs in the homogeneous gas phase, even at relatively oxygen concentrations in the reaction gas, such as are required to maintain a certain level of oxidation of the catalysts. Because of the fact that the temperature after mixing which is preferably from 180° to 290° C, especially from 200° to 270° C, can be regulated efficiently and rapidly, there is also no danger of polymerization of the reaction products, and the dew point is very low since it is not steam but off-gas which is employed as the inert diluent. In addition, a surprising improvement in the yield of acrylic acid and in the selectivity in the second oxidation stage is found with the process according to the invention, and this improvement is not solely attributable to the suppression of the post-combustion of acrolein in the space between the two stages. In contrast to the process of German Published Application No. 2,056,614, in which the air and the off-gas are fed exclusively into the first stage, a gradation of activity of the catalysts in the conventionally used reaction tubes is not essential in the process according to the invention, but can be of advantage. In other respects, the advantages of the process of German Published Application No. 2,056,614, in particular the low ratio — compared to other processes — of steam to acrylic acid in the reaction gas of the second stage, remain preserved, and as a result it is also still possible to use very economical separation processes, e.g. as described in German Printed Application No. 2,136,396.

In the new process, conventional acrolein-selective catalysts are employed, e.g. those disclosed in German Pat. No. 1,268,609, German Printed Application No. 2,038,749 or German Published Application Nos. 2,203,710, 2,133,110, 2,125,032, 1,792,424 and 2,000,425, these specifications being incorporated by reference. These catalysts give a conversion of more than 80 mole% of the propylene employed, in a single pass, at a bath temperature (i.e. at a temperature of the medium surrounding the reaction tubes, which frequently consists of molten salts) of below 380° C, especially at from 180° to 379° C, preferably from 180° to 350° C, and with a residence time (in the tube, of internal diameter from 1.8 to 2.5 cm, which is filled with catalyst beads of conventional type) of up to 4 seconds, preferably from 0.5 to 3.5 seconds, especially from 1 to 3 seconds. Such catalysts in general contain, as the main components, molybdenum, bismuth and iron in an oxidic form, preferably molybdenum, bismuth, iron, nickel and/or cobalt and optionally Be, Mg, Zn, Ba Ca, Sr, Na, K, Rb, Cs, Sn, Cr, Ge, Al, Ga, In, rare earth metals, Nb, Ta, Mn, Re, Pt, Pd, Ru, Rh, Ir, Tl, Ag, U, P, Ti, Sb and/or As and are in general supported on, or mixed with, inert carriers such as silica, silicates, aluminum oxides or hydrated aluminum oxides, titanium dioxide or zirconium oxides. Particularly preferred acrolein-selective catalysts are those of the general composition $Mo_{12}(Ni + Co)_{2-14}Bi_{0.5-6}Fe_{0.5-6}X_{0-8}Y_{0-1}Z_{0-2}O_x$, wherein X is Zn, Mg, Sn, W, Ca, Ba and Ti, Y is Li, Na, K, Rb, Cs, Al, In, Nb, Ta, Ga and La, $x$ is the amount of oxygen correponding to the valency of the elements in the formula, and Z is Ge, P, As, V and Cr, supported on carriers. However, acrolein-selective catalysts which in addition to oxygen contain vanadium and antimony as the main components can also be used.

Such catalysts are acrolein-selective, i.e. they catalyze the oxidation of propylene so as to give very predominantly acrolein; acrylic acid and carbon monoxide and dioxide, as well as maleic acid, acetic acid, formaldehyde and acetone are produced only in very minor amounts, and at times even in traces only.

In the second stage of the new process, catalysts which are selective for acrylic acid are employed, such as are described, e.g., in German Pat. No. 1,908,965, German Published Applications Nos. 1,618,744, 2,164,905, 2,152,037 and 1,924,496 and Published Netherlands Patent Application No. 72/05,595, these specifications being incorporated by reference. These give a conversion of more than 80 mole%, preferably at least 85 mole%, and in particular at least 90 mole% of the acrolein fed in, in a single pass, at a bath temperature below 350° C, especially at from 180° to 349° C, preferably from 180° to 330° C, with a residence time of up to 4 seconds, preferably from 0.5 to 3.5 seconds and especially from 1 to 3 seconds. Such catalysts in general contain, in the form of oxides, molybdenum and vanadium as the main components, but preferably molybdenum, vandadium and one or more elements from amongst tungsten, copper, iron, tin, antimony and chromium and, optionally, minor amounts of alkaline earth metals and alkali metals and/or In and/or Tl as additional components. Preferred catalysts for the second stage are those of the general composition $Mo_{12}V_{0.5-16}W_{0-8}X_{0-12}Y_{0-2}O_x$, wherein X is Cu, Fe, Mn, Sn, Sb and Co, Y is an alkali metal, alkaline earth metal, Zn and/or Cr, and $x$ is the amount of oxygen corresponding to the valency of the elements in the formula, these catalysts being applied to supports.

The fresh propylene fed in may be of technical grade, and may thus, e.g., contain from 5 to 15% by volume of propane. Steam may be added to the gas mixture if desired, e.g. in amount of up to 3 moles per mole of propylene fed in, but the addition of steam is not essential to the process. In the preferred embodiment of the process, the amount of steam fed into the reactors together with the off-gas, the air and the propylene should be less than 2 moles, and in particular less than 1 mole, per mole of propylene fed in. An essential feature of the process of the invention is the use of air as the oxidant, since the nitrogen in the air is the principal inert diluent in the synthesis gas. For this reason, an increased content of steam and/or carbon monoxide and carbon dioxide in the off-gas is not necessary with the process of the invention, in contrast to the process of German Printed Application No. 1,793,302. Accordingly, the off-gas contains nitrogen as the main component, with small amounts of unconverted propylene, oxygen, propane, argon, carbon monoxide, carbon dioxide and, depending on the condensation conditions and the conditions under which the reaction products are washed out of the reaction gas from the second stage, small quantities of solvent vapors and reaction products such as steam, acrolein, acetaldehyde, acetone and acetic acid.

In general, the composition of the off-gas is from 0 to 1.5% by volume, especially from 0.2 to 1.0% by volume, of propylene, from 0 to 5% by volume, especially from 1 to 4% by volume of oxygen, from 0 to 10% by volume, especially from 1 to 7% by volume, of carbon oxides ($CO/CO_2$), from 0 to 1% by volume of propane, from 0 to 1% by volume, especially from 0.1 to 0.5% by volume, of acrolein, from 0 to 10% by volume, especially from 0.5 to 5% by volume, of steam, from 0 to 0.1% by volume, especially from 0.01 to 0.05% by volume, of other organic reaction products and solvents, and from 100 to 71.4% by volume, especially from 97.19 to 81.45% by volume, of nitrogen together with the natural content of rare gases.

The lowest values given for the content of propylene, oxygen and carbon monoxide and carbon dioxide take into account the start-up process of a nitrogen-filled plant. Changes in the upper limit of, e.g., the amount of oxygen, may arise if stripping air from a desorption column which may be used for working up the acrylic acid is admixed to the reaction gas and recycled with the off-gas. However, in general, the composition of the off-gas is within the stated limits even in such a case. In the new process, the portion of the off-gas, from the stage of isolating the acrylic acid, which is not used for mixing with propylene and/or air or the hot reaction gases from the first stage is discarded, but it may also be used for other purposes.

Where the amounts of off-gas and fresh air fed in after the first stage are small, e.g. 10% or a little more, it may be desirable to cool them, e.g. on the delivery side of the compressors, e.g. to temperatures from below 60° C to just above the dew point. In the preferred method of working up, according to German Printed Application No. 2,136,396, the (partially) recycled off-gas has a dew point of from 20° to 40° C after leaving the condensation stage (the stage of isolating the acrylic acid), but if special processes for isolating the acrylic acid are used the dew point may also be above or below these values.

In the new process, it is also possible to admix a part of the off-gas or air to the reaction gases from the second stage immediately after it leaves the catalyst zone, so as to quench the reaction gas to from 150° to 300° C before it enters the condensation stage or wash stage.

The process may be carried out under atmospheric or superatmospheric pressure, pressures of from 1 to 5 atmospheres being preferred.

The liters and cubic meters in the Examples are volumes at 0° C and standard pressure.

EXAMPLE 1

A fixed bed reactor consisting of a bundle of 400 tubes each of 21 mm diameter is fed hourly with a mixture of 34.8 cubic meters of fresh propylene, 240 cubic meters of air and 280 cubic meters of off-gas which contains nitrogen at the main component, together with 0.4% by volume of (unconverted) propylene, 3% by volume of oxygen, 5.8% by volume of carbon monoxide and carbon dioxide and small quantities of uncondensed reaction products, as well as 2% by volume of steam. In the gas mixture entering the reactor, the molar ratio of propylene : oxygen : residual gas is 1 :1.64 : 12.86. The reactor is charged with a conventional acrolein-selective catalyst based on oxides of molybdenum, iron, bismuth, nickel, zinc, phosphorus, silicon and thallium, prepared according to Example 1 of German Published Application No. 2,133,110, in an amount of 0.865 liter per tube. The reaction zone undergoes heat exchange with a salt melt bath kept at 323° C. 95% conversion of propylene takes place in the reaction zone.

The gas mixture, containing acrolein, which leaves the reaction zone is mixed, immediately below the (lower) tube plate, with a mixture of 105 cubic meters of air and 145 cubic meters of off-gas per hour, at 45° C (i.e. with cold gas), the amount corresponding to 32.5% by volume of the total amount of air and off-gas fed to the two reactors. From the amounts of fresh propylene, air and off-gas fed in total to the two reactors, a molar ratio of propylene : oxygen : residual gas of 1 : 2.37 : 19.14 may be calculated. The mixture of off-gas and reaction gas from the first stage, which mixture is at 260° C, is then passed through a second reactor which consists of a bundle of 280 tubes each of 25 mm diameter. The tubes are each filled with 1.23 liters of a catalyst based on oxides of molybdenum, vanadium, iron and tungsten and prepared according to Example 1 of German Pat. No. 1,908,965. The reaction zone undergoes heat exchange with a salt melt kept at 275° C. The acrolein which enters undergoes 95% conversion. Acrylic acid and residual acrolein are separated from the reaction gas from the second reactor by washing out with a mixture of 75% by weight of diphenyl ether and 25% by weight of diphenyl and the residual off-gas, after discarding a proportion, is recycled, in the stated amounts, to points before the two reactors of the first and second stages.

Analysis of the products shows a yield of acrylic acid of 67 mole%, based on fresh propylene fed in; 19.5 mole% of the fresh propylene fed in are converted to carbon monoxide and carbon dioxide.

The yield of acrylic acid remains constant for more than 100 days.

COMPARATIVE EXAMPLE 1a

The same arrangement and the same catalysts as in Example 1 are used. The first reactor is fed hourly with a gas mixture of 34.8 cubic meters of fresh propylene, 212 cubic meters of air and 280 cubic meters of off-gas containing 0.9% by volume of propylene, 1.9% by volume of oxygen, 6.2% by volume of carbon monoxide and carbon dioxide and 2% by volume of steam. This corresponds to a molar ratio of propylene : oxygen : residual gas of 1 : 1.35 : 11.86. The propylene is only converted initially to the extent of 91.5%, even if the salt melt temperature is raised to 340° C. 105 cubic meters of air and 165 cubic meters of off-gas per hour are admixed to the reaction gas; this represents 35.4% by volume of the total amounts of fresh air and off-gas fed in, and the mixture assumes a temperature of 260° C. The amounts of fresh propylene, air and off-gas fed in total to the two reactors correspond to a molar ratio of propylene : oxygen : residual gas of 1 : 2.02 : 18.38. The acrolein formed is converted to the extent of 96% in a second reactor at a salt bath temperature of 275° C.

The yield of acrylic acid, based on fresh propylene fed in, is now only 62.5 mole%, 19.5 mole% being combusted. In the course of 7 days' operation, the propylene conversion and yield of acrylic acid showed a tendency to drop continuously and the combustion to carbon moxoxide and carbon dioxide a tendency to rise.

COMPARATIVE EXPERIMENT 1b

The same catalysts and the same arrangement as in Example 1 are used. In contrast to Example 1, the entire air and the entire off-gas are fed in with the fresh propylene into the first stage only. Because of a large rise in temperature in the space between the two catalysts and in the CO concentration in the off-gas, it is necessary to cut back the propylene throughput considerably or raise the amount of off-gas considerably. Stable running is possible when the first reactor is fed hourly with 14.3 cubic meters of propylene, 150 cubic meters of air and 295 cubic meters of off-gas containing 0.2% by volume of propylene, 1.5% by volume of oxygen, 10% by volume of $CO/CO_2$ and 2% by volume of steam, corresponding to a molar ratio of propylene : oxygen : residual gas of 1 : 2.42 : 27.4 93% of the fresh propylene fed in are converted at a salt melt temperature of 340° C in the first reactor and 275° C in the second reactor. The yield of acrylic acid is 53% and 38.5% of the fresh propylene fed in are combusted. The rise in temperature, in the gas space between the two stages, to above 380° C and the increase in CO concentration show that under the stated conditions post-combustion of acrolein occurs.

EXAMPLE 2

A reactor which consists of a tube of 25 mm diameter is fed hourly with 100 liters of propylene, 1,000 liters of fresh air and 900 liters of off-gas which contains practically only nitrogen and 8.9% by volume of steam. The molar ratio of propylene : oxygen : residual gas is accordingly 1 : 2.1 : 16.9. The tube contains 975 liters of a catalyst based on oxides of molybdenum, iron, bismuth, nickel, zinc, phosphorus, silicon and indium. The tube undergoes heat exchange with a salt melt at 319° C. The propylene undergoes 95% conversion. Immediately after it leaves the catalyst bed of the first stage, the reaction gas is mixed hourly with a mixture of 50 liters of air and 200 liters of off-gas at a temperature of 30° C; this amount corresponds to 11.6% by volume of the total amount of air and off-gas. The mixture assumes a temperature of 290° C. The amounts of propylene, air and off-gas fed in total to the two reactors correspond to a molar ratio of propylene : oxygen : residual gas of 1 : 2.21 : 19.2. The gas mixture is then passed into a second reactor which consists of a tube of 25 mm diameter. This tube contains 975 ccs. of a catalyst based on oxides of molybdenum, vanadium, copper and tungsten, with aluminum oxide as the inert support (empirical formula $Mo_{12}V_3W_{1.2}Cu_{2.4}O_{49.5}$ + 70% by weight, based on total catalyst, of $\alpha$-$Al_2O_3$; the catalyst has a surface area of 2.5 m²/g and is prepared in accordance with Example 1 of Belgian Pat. No. 746,202). The acrolein fed in undergoes 98% conversion at a salt bath temperature of 285° C. From the analysis of the material leaving the second reactor, the yield of acrylic acid is found to be 76 mole%.

COMPARATIVE EXPERIMENT 2a

The same catalysts and the same arrangements as in Example 2 are used. However, in contrast to Example 2, the first reactor is fed with the entire amount of air and off-gas in addition to the fresh propylene, i.e. with 100 liters of propylene, 1,050 liters of air and 1,100 liters of off-gas per hour. The reaction gas mixture leaving the first stage is cooled to 285° C in a heat exchanger, operated with a salt melt and located imeediately after the first stage, and is passed into the second reactor. Under running conditions in other respects identical to Example 2, the yield of acrylic acid is 72 mole%, with 93% conversion of propylene in the first stage and 97% conversion of acrolein in the second stage.

We claim:

1. In a process for the manufacture of acrylic acid by oxidation of propylene with a gas containing molecular oxygen in two spatially separate oxidation stages wherein an acrolein-selective catalyst containing molybdenum, bismuth and iron in an oxidic form which at a bath temperature below 380° C and a residence time of up to 4 seconds is able to produce, in a single pass, a conversion of more than 80 mole% of the propylene employed is used in the first stage, and a catalyst containing molybdenum and vanadium in an oxidic form, which is selective for acrylic acid and which at a bath temperature below 350° C and a residence time of up to 4 seconds is able to produce, in a single pass, a conversion of more than 80% of the acrolein is used in the second stage, and in the oxidation a part of the off-gas, which has been substantially freed from condensable products, including water, and essentially consists of nitrogen and small amounts of unconverted propylene, oxygen, propane and carbon monoxide and carbon dioxide, is fed to the oxidation in addition to fresh propylene and air, the improvement which comprises
   a. feeding the recycled off-gas and air in part to the first oxidation stage and in part to the second oxidation stage,
   b. maintaining the molar ratio of propylene : oxygen : residual gases in the feed to the first stage at 1 :1.5–2.3 : 11–19,
   c. maintaining the molar ratio of the total propylene fed in, to the total oxygen fed in, in the form of air or off-gas, before and after the first stage, and to the total residual gases fed in, at 1 : 1.9–2.5 : 13–25, with the proviso that
   d. the air and recycled off-gas are divided between the two feed points in such a way that from 10 to 50% by volume of the total quantity of air and off-gas fed in is added after the first stage, and
   e. admixing the air and off-gas to the reaction gas mixture after the first stage, immediately after it leaves the catalyst zone, so that the mixture is rapidly cooled to a temperature of from 150° to 320° C.

2. In a process for the manufacture of acrylic acid by oxidation of propylene with a gas containing molecular oxygen in two spatially separate oxidation stages wherein an acrolein-selective catalyst containing molybdenum, bismuth and iron in an oxidic form which at a bath temperature of from 180° to below 380° C and a residence time of up to 4 seconds is able to produce, in a single pass, a conversion of more than 80% of the propylene employed, is used in the first stage, and a catalyst containing molybdenum and vanadium in an oxidic form, which is selective for acrylic acid and which at a bath temperature of from 180° to 349° C and a residence time of from 0.5 to 3.5 seconds is able to produce, in a single pass, a conversion of more than 80% of the acrolein, is used in the second stage and in the oxidation a part of the off-gas, which has been substantially freed from condensable products, including water, and essentially consists of nitrogen and small amounts of unconverted propylene, oxygen, propane and carbon monoxide and carbon dioxide, is fed to the oxidation in addition to fresh propylene and air, the improvement which comprises
   a. feeding the recycled off-gas and air in part to the first oxidation stage and in part to the second oxidation stage,
   b. maintaining the molar ratio of propylene : oxygen : residual gases in the feed to the first stage at 1 : 1.6–2.1 : 12–16,
   c. maintaining the molar ratio of the total propylene fed in, to the total oxygen fed in, in the form of air or off-gas, before and after the first stage, and to the total residual gases fed in, as 1 :2.1–2.4 :16–23 with the proviso that
   d. the air and recycled off-gas are divided between the two feed points in such a way that from 20 to 45% by volume of the total quantity of air and off-gas fed in is added after the first stage, and
   e. admixing the air and off-gas to the reaction gas mixture after the first stage, immediately after it leaves the catalyst zone, so that the mixture is rapidly cooled to a temperature of from 180° to 290° C.

3. A process as set forth in claim 2 wherein said temperature in (e) is from 200° to 270° C.

* * * * *